United States Patent [19]

Tsibris et al.

[11] Patent Number: 4,614,715

[45] Date of Patent: Sep. 30, 1986

[54] PREDICTIVE TEST FOR IMPENDING OVULATION IN MAMMALS

[75] Inventors: John C. M. Tsibris, Hanover Park; William N. Spellacy, Chicago, both of Ill.

[73] Assignee: The Board of Trustees of the University of Illinois, Urbana, Ill.

[21] Appl. No.: 605,982

[22] Filed: Apr. 30, 1984

Related U.S. Application Data

[63] Continuation-in-part of Ser. No. 378,134, May 14, 1982, abandoned.

[51] Int. Cl.$^4$ ............................................... C12Q 1/28
[52] U.S. Cl. .................................... 435/28; 435/810
[58] Field of Search ................. 435/25, 28, 291, 292, 435/296, 810; 436/65, 906; 422/61

[56] References Cited

U.S. PATENT DOCUMENTS 3,472,738 10/1969 Foster .................................... 435/28
4,131,112 12/1978 Kopito et al. ......................... 128/765

FOREIGN PATENT DOCUMENTS

80/022596 11/1980 PCT Int'l Appl. ................... 435/28

OTHER PUBLICATIONS

Tsibris et al, Contraception, 25(1): 59–67, Jan. 1982.
Tsibris et al, J. Clin. Endocrin. Matab., 54(5): 991–997 (1982).
Blain, Contraception, 11(6): 677–680 (1975).
Tenovuo et al, Biochem. Med., 25: 337–345 (1981).
Cockle et al, British I. Obstet. Gyn., 85: 776–782 (1978).
Moghissi, Fertility and Sterility, 34(2): 89–98 (1980).

*Primary Examiner*—Esther M. Kepplinger
*Attorney, Agent, or Firm*—Mathew L. Kalinowski

[57] ABSTRACT

Serial assay of guaiacol peroxidase ($G-P_x$) in the cervical mucus of human females during the menstrual cycle demonstrated that $G-P_x$ levels decrease 20- to 100-fold in the middle of the cycle relative to levels at other times in the cycle. Cervical mucus can be sampled either at the external cervical os or in the vaginal canal. The test for assaying $G-P_x$ includes extracting the sample with a $Ca^{++}$-containing buffer solution at a slightly alkaline pH, and thereafter adding guaiacol and a peroxide. Decreasing levels of $G-P_x$ are indicated by a color change from deep red to pink to yellow. The decrease was found to coincide with the peak of plasma estrogens that normally precedes ovulation. Accordingly, the test provides a reliable prediction of impending ovulation and is therefore useful in the practice of natural fertility control.

7 Claims, 3 Drawing Figures

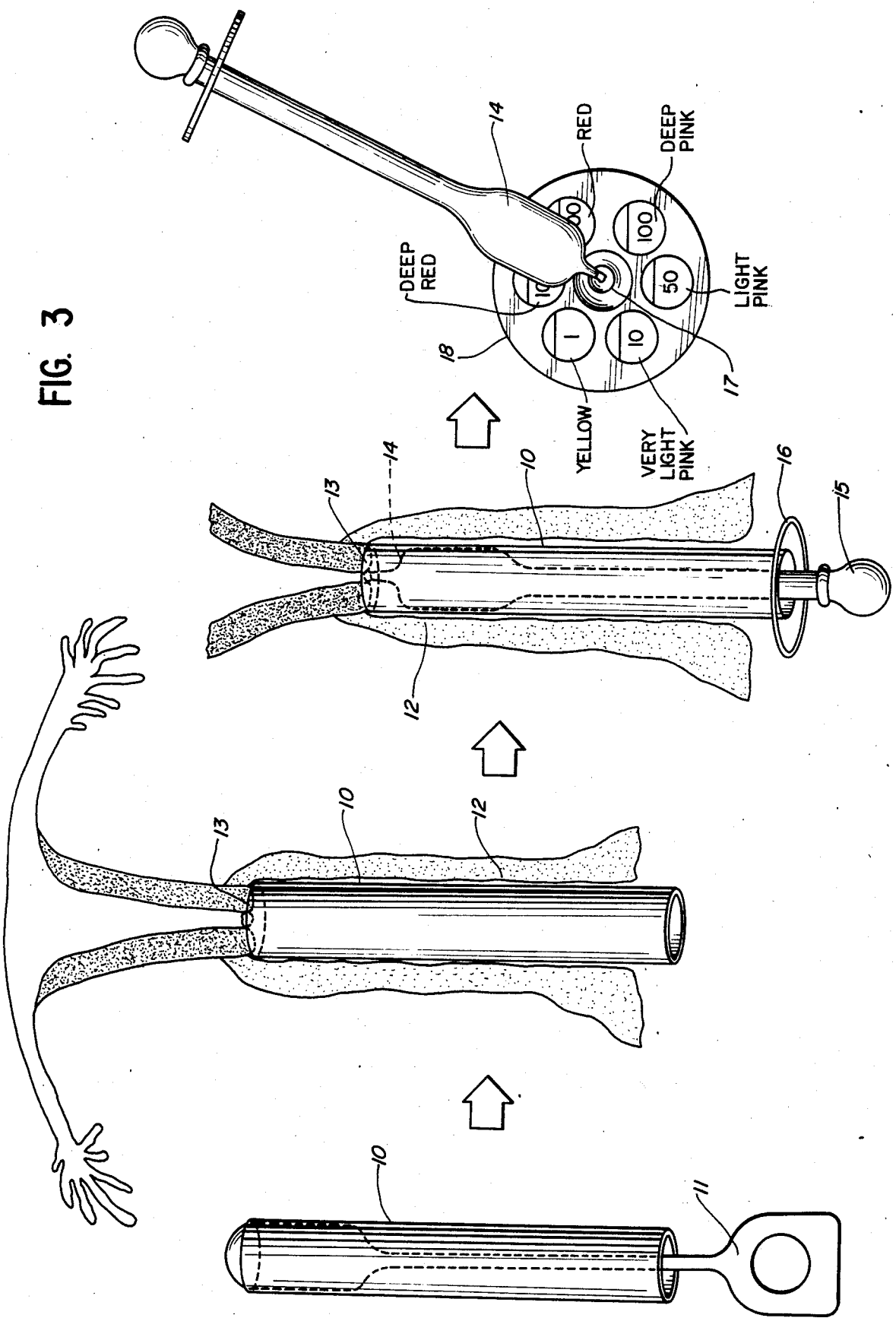

PREDICTIVE TEST FOR IMPENDING OVULATION IN MAMMALS

This application is a continuation-in-part of application Ser. No. 378,134, filed 05/14/82, now abandoned.

This invention relates to a test for predicting impending ovulation in the female. More particularly, this invention relates to a method for assaying guaiacol peroxidase ($G-P_x$) levels in a sample of cervical mucus. In a particular aspect, this invention relates to a simple test that can be easily practiced by a woman at home to provide her with reliable means for natural fertility control.

BACKGROUND OF THE INVENTION

Prediction and detection of ovulation are critical steps in regulating female fertility and in aiding family planning. To this end, a variety of methods have been proposed in the prior art such as, for example, daily assay of the serum or urine for the presence of leutenizing hormone (LH), estrogens, progesterone, and the like. Such techniques, however, are cumbersome, expensive, and require the services of a skilled technician.

The daily recording of basal body temperature (BBT) is a well known method for detecting ovulation. Considerable skill, however, is required in observing and interpreting the data; furthermore, the BBT record does not predict the day of ovulation but rather provides evidence of ovulation two or three days after it has occurred.

Increases in peroxidase activity in the saliva, vaginal fluids, and cervical mucus have been measured as a means for detecting ovulation. Foster, R. O., U.S. Pat. No. 3,472,738 discloses a test for measuring the increase in peroxidase activity in the saliva around the time of ovulation which involves mixing the saliva with guaiacol, hydrogen peroxide, and sodium pyruvate to produce a blue color. More recently, measurement of salivary peroxidases whose activity increases around ovulation has been described by Cockle, S. M. et al., Brit. J. Obstet. Gyneacol. 85, 776–82 (1978) and Tenovuo, J. et al., Biochem. Med. 25, 337–345 (1981).

Vaginal fluids have been reported to react with hydrogen peroxide and a variety of compounds such as aromatic amines, guaiacol, and dyes to produce a blue color which increases in intensity around ovulation (Oster G. et al., International Application No. PCT/US 80/00618).

Blain J. A. et al., Contraception 11, 677–680 (1975) describe a procedure for measuring $G-P_x$ levels in cervical mucus which involves mixing a mucus sample with a phosphate-citrate buffer at pH 6.5 and with relatively large amounts of hydrogen peroxide and guaiacol. $G-P_x$ content of the cervical mucus was measured throughout the menstrual cycle and was found to be at a low level with no change occurring until the final week. The procedure showed no decrease in $G-P_x$ level at the point of incipient ovulation.

Additional techniques for predicting and detecting ovulation are discussed by Moghissi, K. S. Fetility and Sterility, 34, No. 2, 89–98, August 1980, which citation is incorporated herein by reference as illustrative of the state of the art. Moghissi concludes that "Currently no reliable method for prediction of ovulation is available, but a better understanding of cyclic changes in the constituents of cervical mucus and in the pattern of excretion of sex hormone metabolites may lead to the development of improved methods of ovulation detection as well as ovulation prediction."

Accordingly, it is an object of this invention to provide a reliable method for predicting ovulation in the female species based on an assay of $G-P_x$ in cervical mucus or vaginal fluids.

It is another object of this invention to provide a simple test for $G-P_x$ levels in cervical mucus or vaginal fluids that can be easily practiced by a woman at home to provide her with reliable means for natural family planning.

It is still another object of this invention to provide a simple kit for carrying out the inventive test method. These and other objects will become apparent as description of the invention proceeds.

In accordance with this invention, a method for detecting impending ovulation in human female comprises an assay for the decrease in $G-P_x$ levels in cervical mucus at the time of impending ovulation. In the method, a sample of cervical mucus obtained from either the cervical os or the vaginal canal is extracted with an aqueous solution comprising $Ca^{++}$ and a buffer providing a slightly alkaline pH. The extract is admixed with a small amount of guaiacol and peroxide whereupon the presence of $G-P_x$ is indicated by the development of color having maximum absorbance at 470 nm. Daily assays are performed until an abrupt color change signals a significant drop in $G-P_x$ level and the onset of the ovulation process. Although decrease in $G-P_x$ levels coincident with impending ovulation is assayed preferably in samples of cervical mucus, it is understood that the test procedure is applicable to assaying the corresponding changes in salivary peroxidase levels.

A suitable solution for extraction of $G-P_x$ comprises a water soluble calcium salt and a buffer that is non-reactive with $Ca^{++}$ and that provides a slightly alkaline pH. A solution that can be employed to advantage contains 0.5M $CaCl_2$ and 10 mM Tris-Cl buffer at a pH of about 7.2.

Peroxides that can be used include hydrogen peroxide, sodium peroxide, barium peroxide, sodium perborate, and the like. Hydrogen peroxide is generally preferred because of its ready availability, complete water solubility, and ease of concentration control.

For precise clinical assay, changes in $G-P_x$ levels during the menstrual cycle can be followed by absorbance measurements at 470 nm with a spectrophotometer. The decrease in $G-P_x$ levels from about 1000 to 100 to 1 units is associated with a visual color change from deep red to pink to yellow. A level of about 100 units or a color change from deep red to pink indicates impending ovulation and the onset of the fertile period. That period of the cycle is ended when the assay again shows a deep red color.

DESCRIPTION OF THE PREFERRED EMBODIMENTS

The invention is further illustrated by reference to the following procedures and examples.

Materials. Tris-Cl buffer containing $Ca^{++}$ was prepared by dissolving $CaCl_2$ in water to provide a 0.5M concentration, tris(hydroxymethyl)aminomethane to provide a concentration of 10 mM, and HCl to provide a pH of 7.2.

Guaiacol was dissolved in the Tris-Cl buffer in amount to provide a concentration of 13 mM.

$H_2O_2$ (3%) was diluted with Tris-$Ca^{++}$ solution to provide a concentration of 0.3 mM.

Method. Seven healthy women volunteered for this study. A sample of cervical mucus was collected daily from the cervical os in 1 ml preweighed plastic Tuberculin syringes. Serial blood samples were also drawn. The women recorded daily their basal body temperature. For volunteer D a sample of mucus was also collected daily with a cotton swab from the vaginal canal.

The mucus, weighing 5–500 mg, was stored at $-20°$ C. For assay, 2–6 ml of $Ca^{++}$–Tris-Cl buffer was added to extract soluble and particulate G-$P_x$. The suspension was homogenized at 0° C. in a glass homogenizer with a Teflon pestle at 1500 rpm (10 up-down strokes) and centrifuged at 3000 g for 10 minutes. The supernatant solution was assayed for G-$P_x$ in quadruplicate at 23°–24° C. The final volume for each assay was 1 ml and the reagents were added in the order: $Ca^{++}$–Tris-Cl buffer, 10–300 $\mu$l G-$P_x$ extract, and guaiacol solotion. The reaction was started by adding $H_2O_2$ solution and the rate of guaiacol oxidation was determined by the initial increase in absorbance at 470 nm in a Lambda 3 Perkin-Elmer spectrophotometer. The G-$P_x$ content was expressed as units of activity per gram of wet cervical mucus. A G-$P_x$ unit is defined as the amount of G-$P_x$ needed to catalyze the increase of one aborbance unit at 470 nm per minute. The following hormones were measured by radioimmunoassay: 17$\beta$-estradiol, progesterone, leutenizing hormone, and follicle stimulating hormone.

Figure 1:
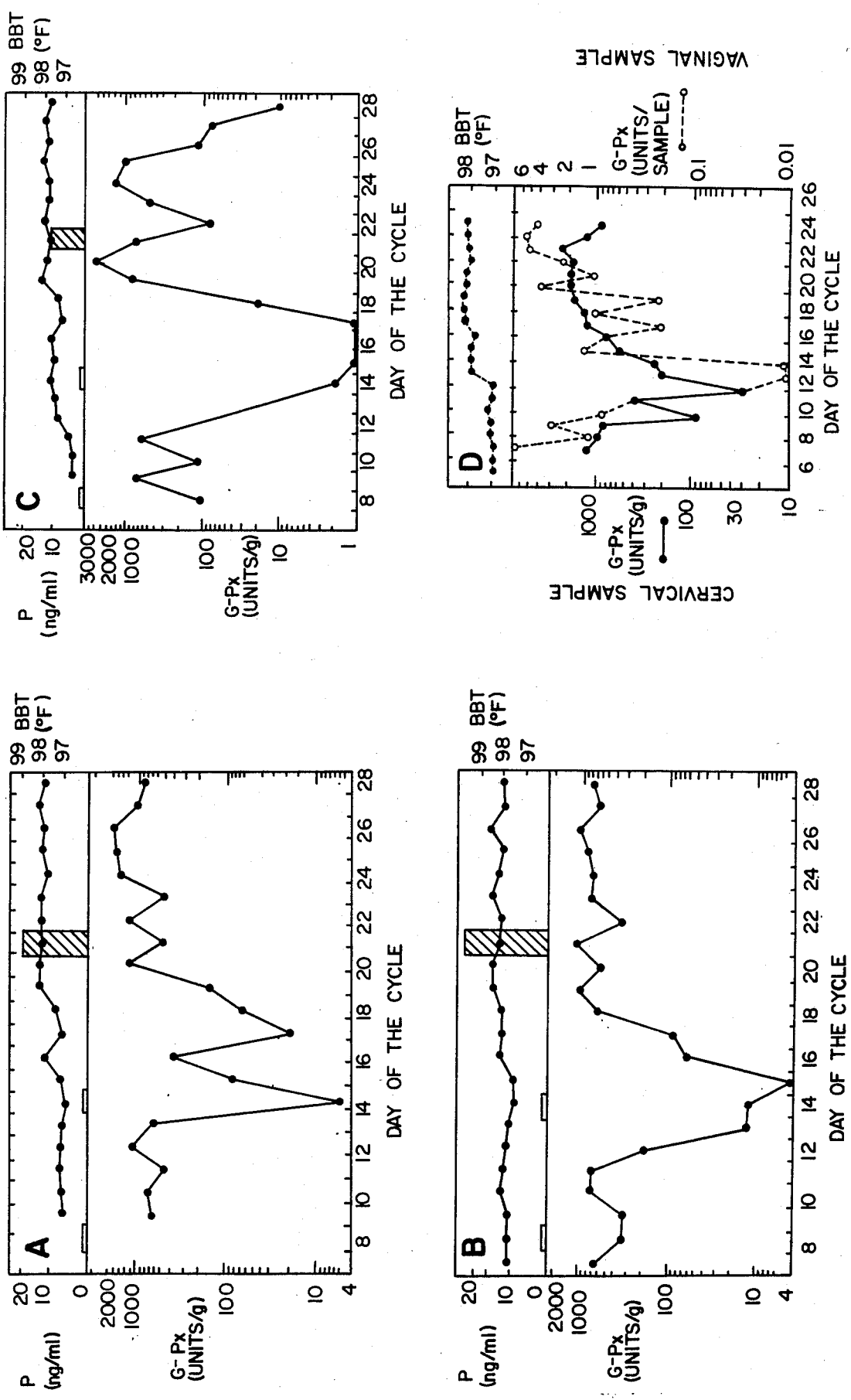
FIG. 1 illustrates the $G-P_x$ content of cervical mucus, basal body temperature (BBT), and plasma progesterone (P) during the menstrual cycle of human volunteers A, B, and C. For human volunteer D, $G-P_x$ levels are shown in mucus samples taken from the cervix and from the vagina.

The data obtained for volunteers A, B, C, and D are shown in FIG. 1. The G-$P_x$ level of volunteer A decreased after day 12 but showed a spike in the middle of the cycle. For volunteers B and C G-$P_x$ levels decreased 5- to 10-fold from day 11 to day 12, remained low for the next 4-5 days, and increased thereafter. The G-$P_x$ level of volunteer D also showed an abrupt drop from day 11 to day 12 for both the mucus samples collected from the cervix and the vagina. The rise in plasma progesterone shown for volunteers A, B, and C provides evidence that ovulation did occur.

Figure 2:
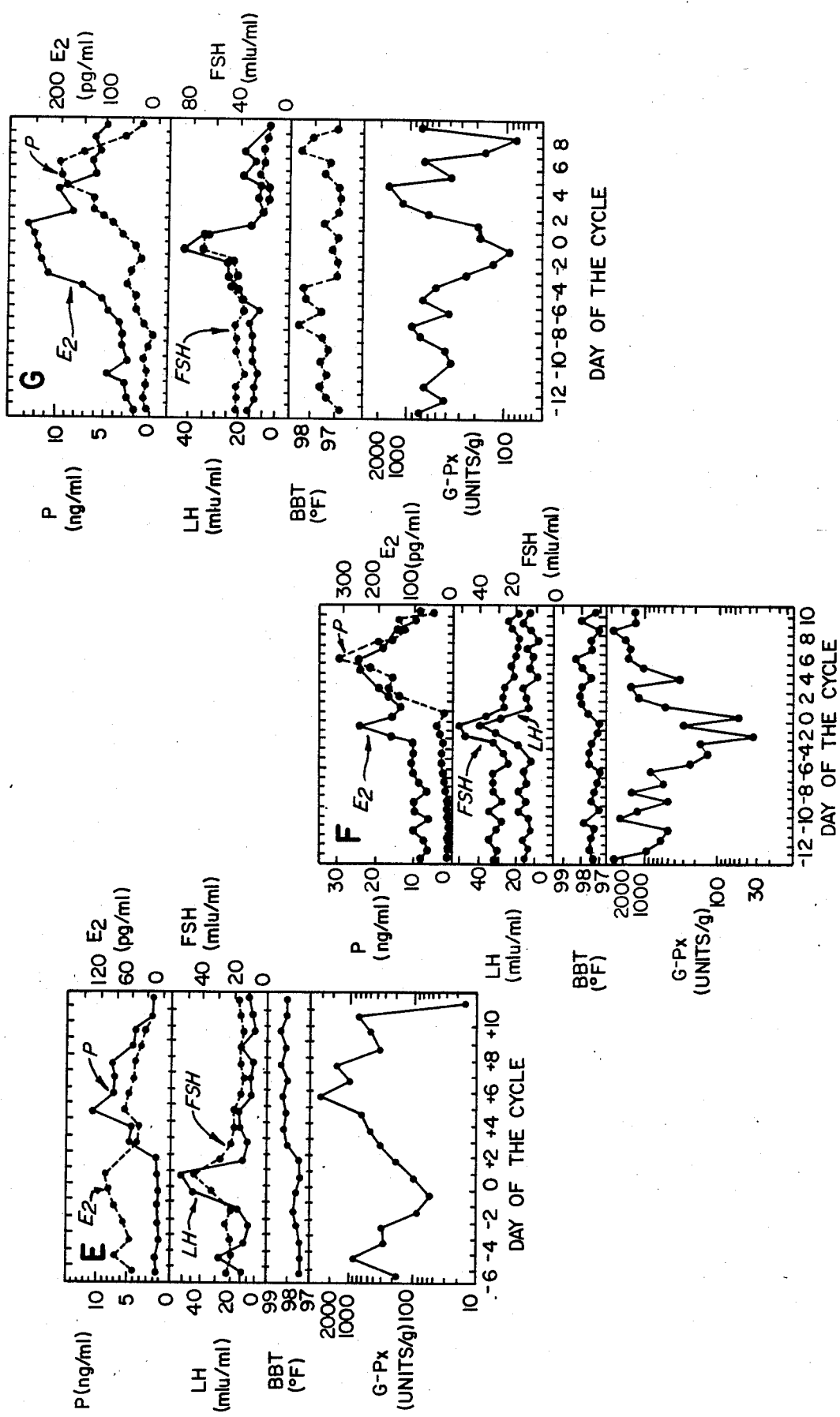
FIG. 2 illustrates the $G-P_x$ content of cervical mucus, basal body temperature (BBT), and plasma leutenizing hormone (LH), follicle stimulating hormone (FSH), progesterone (P), and 17β-estradiol ($E_2$) during the menstrual cycle of human volunteers E, F, and G.

The data obtained for volunteers E, F, and G are shown in FIG. 2. Decreases in G-$P_x$ levels were observed similar to those shown in FIG. 1. In addition, minimum G-$P_x$ content for volunteers E, F, and G was observed to occur approximately one day before the LH, FSH, and $E_2$ peaks. The subsequent increase in progesterone levels again indicated that the ovulation did occur.

Thus, the data obtained in this study indicate clearly that the decrease in G-$P_x$ levels in mucus samples obtained either from the cervix or from the vaginal canal provides three or more days prediction of ovulation in the human female and the procedure provides a woman with a simple, non-invasive means for natural fertility control: she can either abstain from unprotected intercourse for a few days or optimize the time for intercourse if conception is desired.

The herein described procedure for predicting ovulation can also be applied to advantage to female animals whose cervical mucus exhibits hormanal content and changes during estrus similar to those observed in the human female. For example, it is known that in female bovine animals the pre-ovulatory and post-ovulatory changes in reproductive hormones such as progesterone, estrogen, follicle stimulating hormone, and leutenizing hormone, follow very closely the changes that occur in the human female. Accordingly, the inventive procedure is particularly applicable to cattle and dairy cows for the timing of artificial insemination. Additionally, the procedure can be highly useful for (1) identifying the "silent" periods of estrus; (2) timing of both human and animal embryo transfers; and (3) timing of artificial insemination of wild mammals in captivity.

Although this invention has been disclosed in detail with particular reference to certain preferred embodiments thereof, it is understood that variations and modifications can be effected within the spirit and scope of the appended claims. It is intended that all material contained in the above description and figures shall be interpreted in an illustrative and not in a limiting sense.

What is claimed is:

1. A method for predicting impending ovulation in human females using a serial assay for guaiacol peroxidase levels in cervical mucus comprising obtaining a sample of cervical mucus, extracting said sample to provide a guaiacol peroxidase component and assaying said guaiacol peroxidase contained therein, said guaiacol peroxidase showing an abrupt decrease in guaiacol peroxidase level at the time of impending ovulation.

2. The method of claim 1 wherein the cervical mucus is sampled at the external cervical os.

3. The method of claim 1 wherein the cervical mucus is sampled in the vaginal canal.

4. The method of claim 1, 2, or 3 wherein the assay for guaiacol peroxidase produces a color having principal absorbance at 470 nm, said color being of minimal intensity at the time of impending ovulation.

5. The method of claim 1, 2, or 3 wherein the extraction of guaiacol peroxidase comprises the step of extracting the cervical mucus sample with an aqueous solution comprising $Ca^{++}$ and a buffer, the buffer providing a pH of not less than 7.0.

6. The method of claim 5 wherein the the cervical mucus extract is admixed with guaiacol and a peroxide.

7. The method of claim 6 wherein the $Ca^{++}$ concentration is about 0.5M, the buffer is Tris-Cl providing a pH of about 7.2, and the peroxide is $H_2O_2$ in concentration of about 0.3 mM.

* * * * *